United States Patent [19]

Thijs et al.

[11] Patent Number: 5,163,919
[45] Date of Patent: Nov. 17, 1992

[54] OBTURATING MEANS FOR CONTAINER FOR PHARMACEUTICAL AND MEDICAL PREPARATION

[75] Inventors: Anita Thijs, Alken; Willy Van De Poel, Herk-De-Stad, both of Belgium

[73] Assignee: Helvoet Pharma N.V., Alken, Belgium

[21] Appl. No.: 490,587

[22] PCT Filed: Aug. 25, 1989

[86] PCT No.: PCT/BE89/00040

§ 371 Date: Feb. 22, 1990

§ 102(e) Date: Feb. 22, 1990

[87] PCT Pub. No.: WO90/02150

PCT Pub. Date: Mar. 8, 1990

[30] Foreign Application Priority Data

Aug. 25, 1988 [BE] Belgium .................... 08800966

[51] Int. Cl.$^5$ .................... A61M 5/32
[52] U.S. Cl. .................... 604/199; 604/218; 525/332.3; 218/DIG. 4
[58] Field of Search .................... 604/199, 218; 525/332.3; 215/DIG. 3, DIG. 4, 247

[56] References Cited

U.S. PATENT DOCUMENTS

| | | | |
|---|---|---|---|
| 3,198,368 | 8/1965 | Kirkland et al. | 215/DIG. 3 |
| 3,760,969 | 9/1973 | Shimamoto et al. | 215/37 R |
| 4,187,149 | 2/1980 | Tolbert et al. | 195/104 |
| 4,316,941 | 2/1982 | Eguchi et al. | 428/421 |
| 4,321,306 | 3/1982 | Eguchi | 428/421 |
| 4,366,912 | 1/1983 | Matukura et al. | 215/247 |
| 4,381,779 | 5/1983 | Margulies | 604/202 |
| 4,397,903 | 8/1983 | Allen et al. | 428/156 |
| 4,491,653 | 1/1985 | McGinniss et al. | 525/356 |
| 4,500,685 | 2/1985 | Ogawa et al. | 525/343 |
| 4,600,651 | 7/1986 | Aufdermarsh et al. | 428/422 |
| 4,614,276 | 9/1986 | Ihara et al. | 215/364 |
| 4,997,423 | 3/1991 | Okuda et al. | 604/230 |

FOREIGN PATENT DOCUMENTS

| | | | |
|---|---|---|---|
| 0205312 | 12/1986 | European Pat. Off. | |
| 0264273 | 4/1988 | European Pat. Off. | |
| 0338671 | 10/1989 | European Pat. Off. | 604/199 |
| 3415381 | 11/1985 | Fed. Rep. of Germany | |
| 3506766 | 12/1985 | Fed. Rep. of Germany | |
| 0200649 | 11/1984 | Japan | 215/DIG. 2 |

OTHER PUBLICATIONS

Encyclopedia of Polymer Science and Technology, vol. 5, Herman F. Mark, pp. 414-421.
Polymer Science Dictionary, Mark. S. M. Alger, pp. 71 and 331.

Primary Examiner—C. Fred Rosenbaum
Assistant Examiner—Mark O. Polutta
Attorney, Agent, or Firm—Pennie & Edmonds

[57] ABSTRACT

An obturating structure and a container provided with such an obturating structure and a syringe comprising a slidable obturating structure acting as a stopper; and a process for treating an obturating structure prepared at least from one elastomeric material and intended for a static or dynamic seal of a container holding a pharmaceutical or medical preparation, in which process at least the elastomeric part of the obturating structure is at least partially subjected to a treatment with elementary halogen or chemical compound(s) containing reactive halogen.

16 Claims, 2 Drawing Sheets

OBTURATING MEANS FOR CONTAINER FOR PHARMACEUTICAL AND MEDICAL PREPARATION

BACKGROUND OF THE INVENTION

The preparation of materials for pharmaceutical and medical use requires the utmost care. Such materials may be used for medication of humans or animals, as well as for various related purposes, such as the diagnosis of disorders of humans and animals.

If the materials deviate from the required quality standard, they may exert obnoxious or even fatal influence on the treated being or lead to equally dangerous wrong conclusions in for instance a diagnosis.

The preparation of such materials is entrusted to qualified pharmacists. They generate the materials in the required quality by using appropriate equipment and procedures in carefully constructed premises.

The materials, once prepared, must however be stored in containers in order to allow their transport to the application site. Between preparation and application, a considerable time interval may elapse. It is clear that the container must be such that no appreciable deterioration of the materials takes place.

Container systems for the purpose of storage of the materials have been elaborated in the past three or four decades for a very large number of applications. In many cases, the container system not only preserves the good quality of the packed material but additionally facilitates or even makes possible its actual application.

Many systems employ elastomeric (rubber) components, functioning practically always as a sealing means between the container content and the environment, and additionally also in many cases as a means for easy and/or safe application.

Two typical examples from a very large body are the following

1. A glass vial containing a fluid intended for parenteral medication is closed with a soft elastomeric stopper. The stopper allows penetration with a hypodermic needle or a spike. The sterile fluid may then be withdrawn from the vial without actually opening it, thus avoiding the danger of contamination with microorganisms or other undesirable matter.

2. A glass tube is used as a parenteral fluid cartridge by closing one end with an elastomeric stopper in the shape of a plunger. The other end is connected to a hypodermic needle. The fluid content of the cartridge can be pushed out through the needle by pushing the elastomeric plunger with a suitable plunger rod. In this application, the elastomeric part must form a static seal during shelf life of the cartridge and a dynamic seal during the actual application. In the latter stage, it must slide very smoothly in order to allow correct medical action.

From the above, it will be clear that elastomeric seals in this area may have a very wide variety of shapes and dimensions. In the following text they will be addressed as "elastomeric seals" for short.

In the course of the last three decades, much work has been devoted to the development of suitable materials for elastomeric seals in this field. The work was complex because elastomeric materials for the production of seals are composed themselves over a number of starting materials. Such starting materials must be most carefully selected as well as combined in accurately balanced ratios in order to obtain seals possessing a complex of properties required for the application.

Said seals having the ability to form a static, and if required, dynamic gas- and liquidtight seal for a container containing pharmaceutical or medical preparation (1), very low, and indeed pharmaceutically acceptable, release of extraneous material to the pharmaceutical or medical preparation (2), and durability or persistence of the required properties during the storage time of the container with a pharmaceutical or medical preparation (3), must additionally have, in order to be suitable to be used in equipment for filling or closing containers, the following properties ability to support currently practiced technical treatments for surface cleaning and sterilization (4), and ability to be processed in current technical container filling and closing equipment (5).

By selecting suitable elastomeric base materials and further components, compounds may be obtained which, after curing in an appropriate shaping treatment, have a good balance of properties (1), (2) and (3). Such compounds are proprietary to the pharmaceutical rubber industry.

It has been observed that their final processing, especially on a large scale, in fast running modern machines, requires a certain adaptation of their surface state. By their nature, elastomeric objects have a relatively high coefficient of friction, for instance 2.4. This hampers their ability to be transported in filling equipment and similar machinery and, as a consequence, such equipment must be adapted in complicated and mostly costly ways.

In order to overcome this problem, the elastomeric seals in many cases are coated with some lubricant, for instance silicone oil. Such treatment is additionally favorable in preventing the seals from sticking to one another, which also is a frequently observed phenomenon in uncoated seals, especially after treatment in cleaning, cleansing, sterilization and drying equipment.

However, the silicone oil or other lubricant spoils some desirable properties of the seals as an extraneous material, it contaminates the pharmaceutical or medical material stored in the container. In the case of silicone oil, for instance, it has been observed that a water-based medical preparation after contact with the silicone oil treated elastomeric seal, contains a relatively large quantity of silicone oil droplets in emulsified state.

Coatings with various materials have been proposed, but they generally involve the already mentioned or other drawbacks, for instance a decreased sealing capacity or a high application cost.

The present invention purports to resolve the problem by applying a relatively simple and at the same time cost-efficient treatment, consisting of introducing in a carefully controlled way an amount of halogen atoms into the seal surface. The treated seals acquire the necessary low friction coefficient and lose their aggregation tendency, even upon stringent cleaning, cleansing, sterilizing and drying treatment. They do not lose the desirable properties they already possess before the treatment and release a very low amount of extraneous material to a pharmaceutical or medical preparation.

BRIEF DESCRIPTION OF THE INVENTION

The invention relates to an obturating means prepared at least from one elastomeric material, said means being intended for a static and/or dynamic seal of a container intended to contain a pharmaceutical or medical preparation, in which at least the elastomeric part of the obturating means is at least partially subjected to a treatment with elementary halogen or chemical compound(s) containing reactive halogen atoms so that said obturating means has at least the following properties ability to form at least a static gas- and liquidtight seal for the container;

very low release of extraneous material to the pharmaceutical or medical preparation;

compatibility with the pharmaceutical or medical preparation;

ability to support currently practiced technical treatments for surface cleaning and sterilization and ability to be processed in current technical container filling and closing equipment.

The obturating means according to the invention is preferably treated with fluorine.

In an embodiment of the obturating means according to the invention, the elastomeric part thereof is at least partially treated with a fluorine gas after being washed.

A preferred obturating means according to the invention is obtained by treating the elastomeric part thereof with fluorine gas under a pressure of at least $10^5$ Pa, preferably under a pressure comprised between $10^5$ and $5.10^5$ Pa, during at least 60 seconds, preferably from 60 to 900 seconds, and at a temperature comprised between 15° and 25° C.

The fluorine gas is advantageously mixed with an inert gas and preferably with nitrogen. Such a mixture contains, for example, 1 to 10% fluorine gas and 90 to 99% nitrogen gas.

The invention relates also to a container intended for pharmaceutical or medical preparation, said container being provided with an obturating means according to the invention, and a syringe intended for the injection of pharmaceutical or medical preparation, said syringe containing a slidable obturating means according to the invention, said means acting as a stopper.

The invention relates also to a process for treating obturating means prepared from at least one elastomeric material, said means being intended for a static or dynamic seal of a container for pharmaceutical or medical preparation. In said process, at least the elastomeric part of the obturating means is at least partially subjected to a treatment with elementary halogen or chemical compound(s) containing reactive halogen so as to obtain an obturating means according to the invention.

Rubber obturating means according to the invention as well as a process according to the invention will be described hereafter with reference to the attached drawings which show embodiments of obturating means according to the invention.

DESCRIPTION OF THE PREFERRED EMBODIMENTS

Figure 1:
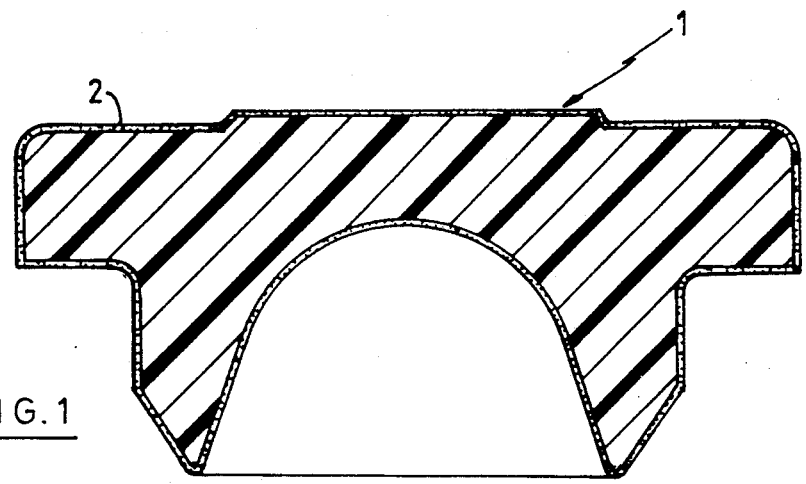
FIG. 1 is a cross-sectional view of a vulcanized obturating means according to the invention.

Obturating means according to the invention are prepared from at least one elastomeric material. Obturating means according to the invention are for example elastomeric stoppers for containers with a pharmaceutical or medical preparation or elastomeric slidable stoppers of syringes intended for injecting pharmaceutical or medical preparation.

Rubber is the generic name for a class of materials composed essentially of one or more elastomeric materials such as polyisoprene, copolymer of isobutene and isoprene, copolymer of butadiene and acrylonitrile, polydimethylsiloxane. Said elastomeric materials may contain functional atoms or molecule groups, introduced before or after the polymerization. Non-elastomeric substances may be added to the elastomer in order to tailor the properties of the material to specific needs. Such substances are for instance finely powdered and purified minerals (example bentonite clay), reactive chemicals intended to enable a crosslinking chemical reaction in the material after it has been converted into the desired shape.

During the manufacturing process (information thereon is given for example in Rubber Technology and Manufacture edited by C. M. BLOW published for the Institution of the Rubber Industry BUTTERWORTHS LONDON—1971), the various components for a given material are mixed to give a malleable compound. This compound is then converted into the desired shape. The material of the final product is characterized by the fact that it is capable of recovering from large deformations quickly and forcibly. It will retract within 1 minute to less than 1.5 times its original length after being stretched at room temperature (18° to 29° C.) to twice its length and held for 1 minute before release.

The following table gives an example of composition of rubber:

|  | % by weight |
| --- | --- |
| chlorobutyl rubber | 50 to 55 |
| vulcanizing agent | 0.5 to 2 |
| filler (silicate) | 40 to 45 |
| zinc oxide | 1 to 3 |
| stearine acid | 0.5 to 2 |
| paraffine oil | 0.5 to 2 |
| colorant (iron-, titane oxide) | 0 to 2 |
| polyethylene wax | 0.5 to 3 |

The process according to the invention may be applied to obturating means composed of at least rubber or elastomeric material as described in the following examples, given as examples only.

EXAMPLE 1

Said process comprised the following steps:

1. The obturating means were washed in a rotary drum, first with warm water and a neutral detergent, then with filtered water and finally with pyrogen-free water.

2. The obturating means were then dried by means of hot filtered air.

3. The obturating means were contacted in a rotary drum with fluorine which was mixed with nitrogen. The mixture of gases contained 1% fluorine and 99% volume nitrogen.

The contact time of the obturating means with fluorine was 900 seconds.

The obturating means were contacted with said mixture of gases at a temperature of 25° C. and under a pressure of $5.10^5$ Pa.

4. The obturating means were washed with water and dried with hot filtered air.

EXAMPLE 2

Said process comprised the following steps:
1. The obturating means were washed in a rotary drum, first with warm water and a neutral detergent, then with filtered water and finally with pyrogen-free water.
2. The obturating means were then dried by means of hot filtered air.
3. The obturating means were contacted in a rotary drum with fluorine which was mixed with nitrogen. The mixture of gases contained 10% fluorine and 90% volume nitrogen.

The contact time of the obturating means with fluorine was 60 seconds.

The obturating means were contacted with said mixture of gases at a temperature of 15° C. and under a pressure of $10^5$ Pa.

4. The obturating means were washed with water and dried with hot filtered air.

Due to the fluorination of the vulcanized rubber product, for example a stopper 1, it is possible with the process according to the invention to obtain a product which has at least one surface 2 which has at least partially been chemically modified up to a certain depth, said depth being at least 10 nanometers ($10^{-8}$m) and having a low friction coefficient and a low aggregation tendency, and which at most may cause a low particles contamination of pharmaceutical or medical materials in contact therewith.

The following table lists typical values and observations deducted from a body of experimental findings and demonstrating the effectiveness of the treatment according to the invention.

TABLE

| Treatment | Findings after additional washing and sterilizing treatment according to BS 3263: 1960 | | | Findings after contacting the seals with water under steam sterilization conditions (30-121° C.)* |
|---|---|---|---|---|
| | friction coefficient** | aggregation | processing in packaging equipment | emulsion density particles ≧ 2 μ per ml of the contact fluid |
| none | 2.4 | tendency to aggregate | not possible | 2000 |
| coating with silicone oil 350 cSt 20 micrograms per cm² | 1.1 | very slight tendency to aggregate | easy | 50 000 |
| according to the invention | 1.1 | no tendency to aggregate | very easy | 500 |

*1 cm² of rubber surface was in contact with 2 ml of particle free water.
**determined in comparable circumstances.

The table shows that the contamination due to the vulcanized rubber treated by the process according to the invention is 100 times lower than the contamination due to rubber covered with a silicone layer.

The man skilled in the art was not able to predict that it was possible to obtain obturating means having the following properties:
ability to form at least a static, preferably a static and dynamic, gas- and liquidtight seal for the container;
very low release of extraneous material to the pharmaceutical or medical preparation as exemplified in the table;
compatibility with pharmaceutical or medical preparation;
ability to support currently practiced technical treatments for surface cleaning and sterilization, and
ability to be processed in current technical container filling and closing equipment;
only by treating the obturating means according to the invention.

The man skilled in the art who tried to avoid contamination of pharmaceutical or medical preparation with particles of the obturating means had the preconceived idea that it was necessary to add a coating on the obturating means so as to make a barrier between the obturating means and the pharma- ceutical or medical preparation. (For example, see European patent application 0 264 273 or U.S. Pat. No. 4,808,453).

Figure 2:
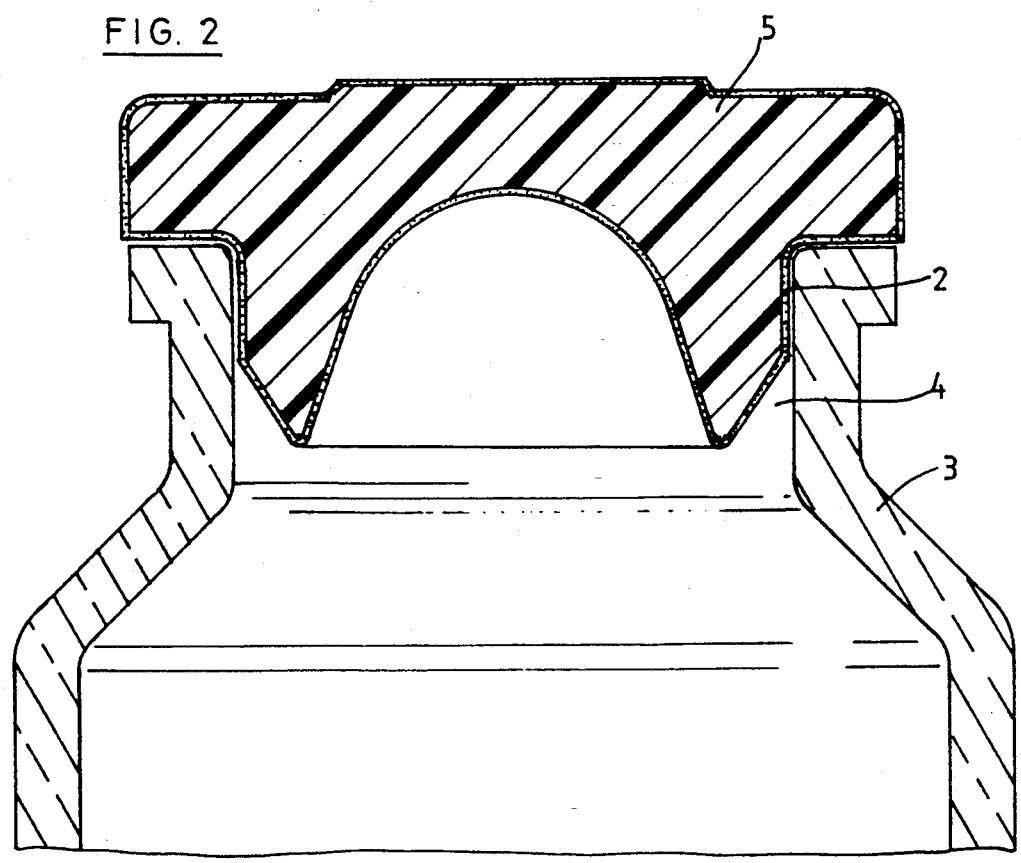
FIG. 2 is a partial cross-sectional view of a vial provided with a vulcanized obturating stopper.

FIG. 2 shows a vial 3 which is provided with an opening 4 which is sealed by a stopper 5 made of rubber and treated by the process according to the invention. Said vial is suitable for containing pharmaceuticals, for example cephalosporine.

The sealing of opening 4 is perfect since the fluorinated surface 2 takes the form of the opening 4 and since said surface 2 consists of a homogeneous and regular layer which is strongly bonded to the stopper.

Figure 3:
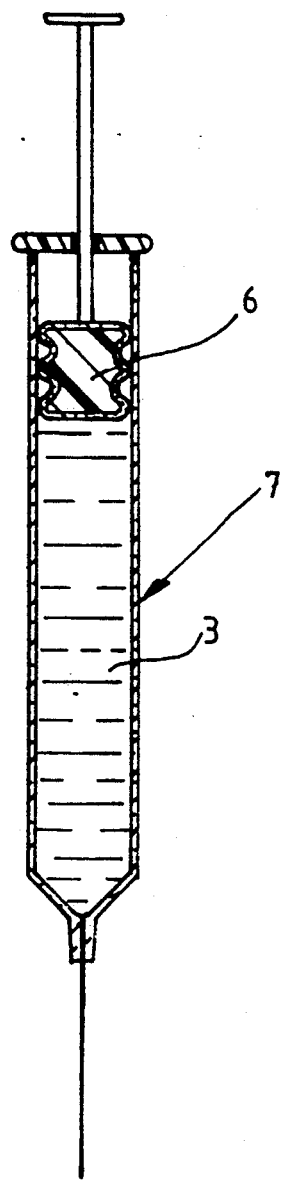
FIG. 3 is a cross-sectional side view of a slidable stopper of a syringe, together with the syringe itself.

FIG. 3 shows a rubber stopper 6 for sealing a syringe 7 which may be previously filled with a pharmaceutical or which may be used for extracting a pharmaceutical from a vial and for injecting it to a patient.

The fluorinated surface of said stopper 6 allows that only a low working force has to be exerted on the stopper during the injection. This force is not increased after storing, for example, a syringe filled 3 years before using it.

Due to the absence of silicones which previously were necessary in order to guarantee the sliding of the stopper, there is no more contamination of the pharmaceutical with particles.

Due to the fact that the surface of the rubber products treated by the process according to the invention is more hydrophobic, there is less interaction between the rubber and the pharmaceuticals which are in contact therewith. The transfer of rubber ingredients to the pharmaceuticals is thereby reduced so that the rubber products according to the invention have a better compatibility.

The surface 2 of rubber products treated by the process according to the invention has a repelling force for dust so that said dust is not able to be deposited on said surface 2. Said dust is thus not able to contaminate the stopper 5 even if said stopper is stored in an environment slightly contaminated with particles during a long time.

In the obturating means according to the invention, a part thereof may not be subjected to a treatment with elementary halogen or chemical compound(s) containing reactive halogen atoms, said means being provided with an untreated surface which is not intended to be in contact with a pharmaceutical or medical preparation.

What we claim is:

1. An obturator for sealing a container for medical or pharmaceutical preparations, said obturator formed of chloro butyl rubber wherein at least a portion of a surface of said obturator is fluorinated upon contact thereof with a fluorine-containing gas such that said fluorinated portion extends to a depth within said obturator of at least about 10 nanometers, said fluorinated surface having a substantially reduced degree of reactivity with said medical and said pharmaceutical preparations in contrast to a corresponding surface which has not been fluorinated.

2. A method for forming an obturator adapted for sealing a container for medical or pharmaceutical preparations, which method comprises:

forming an obturator configured and adapted for sealing a container for a medical or a pharmaceutical preparation from chloro butyl rubber; and contacting a surface portion of said obturator with a fluorine-containing gas so as to fluorinate at least a portion of said contacted surface.

said fluorinated surface having a substantially reduced degree of reactivity with respect to said medical and said pharmaceutical preparations in contrast to a corresponding surface which has not be fluorinated.

3. The method of claim 2 which further comprises contacting said obturator surface with said fluorine-containing gas at a pressure of at least about $10^5$ Pa.

4. The method of claim 3 wherein said pressure ranges between about $10^5$ and $5 \times 10^5$ Pa.

5. The method of claim 3 which further comprises contacting said obturator surface portion with said fluorine-containing gas for at least about 60 seconds.

6. The method of claim 5 wherein said obturator surface portion is contacted with said fluorine-containing gas for between about 60 and 900 seconds.

7. The method of claim 2 which further comprises contacting said obturator surface with said fluorine-containing gas at a temperature of between about 15°-25° C.

8. The method of claim 2 which further comprises adding an inert gas to said fluorine-containing gas.

9. The method of claim 8 wherein said inert gas is nitrogen.

10. The method of claim 9 wherein said obturator surface is contacted with a fluorine-containing gas comprising from about 1 to 10% fluorine gas and from about 90 to 99% nitrogen gas.

11. The method of claim 2 which further comprises washing at least a portion of said obturator prior to contacting said portion with the fluorine-containing gas.

12. A method for forming an obturator adapted for sealing a container for medical or pharmaceutical preparations, which method comprises:

forming an obturator configured and adapted for sealing a container for medical or pharmaceutical preparations from chlorobutyl rubber;

washing at least a portion of a surface of said obturator;

drying said washed surface portion; and contacting said surface portion of said obturator with a gaseous reagent comprising from about 1 to 10% fluorine gas and 90 to 99% nitrogen under a pressure of between about $10^5$ and $5 \times 10^5$ Pa. for between about 60 to 900 seconds at a temperature of between about 15°-25° C. so as to at least partially fluorinate said contacted surface portion to a depth of at least about 10 nanometers, said fluorinated surface having a substantially reduced degree of reactivity with respect to said medical and said pharmaceutical preparations in contrast to a corresponding surface which has not been fluorinated.

13. Container means for storing medical or pharmaceutical preparations, said container means comprising an obturator produced by the process of claim 12.

14. Container means for storing medical or pharmaceutical preparations, said container means comprising an obturator produced by the process of claim 11.

15. A syringe adapted for injecting medical or pharmaceutical preparations, said syringe comprising a slidable obturator formed according to the process of claim 12 to serve as a stopper within said syringe.

16. A syringe adapted for injecting medical or pharmaceutical preparations, said syringe comprising a slidable obturator formed according to the process of claim 12 to serve as a stopper within said syringe.

* * * * *